United States Patent [19]

Suga

[11] Patent Number: 5,314,693
[45] Date of Patent: May 24, 1994

[54] PEST CONTROL CHEMICALS AGAINST PINE WOOD NEMATODES

[75] Inventor: Takayuki Suga, Hiroshima, Japan

[73] Assignee: Kioritz Corporation, Tokyo, Japan

[21] Appl. No.: 12,588

[22] Filed: Feb. 3, 1993

[30] Foreign Application Priority Data

Feb. 7, 1992 [JP] Japan .................................. 4-022203
Dec. 11, 1992 [JP] Japan .................................. 4-331755

[51] Int. Cl.$^5$ ...................... A01N 65/00; A01N 31/08;
A01N 29/04; A01N 27/00
[52] U.S. Cl. ................................ 424/196.1; 514/456;
514/731; 514/755; 514/766; 514/919;
424/DIG. 10
[58] Field of Search ......... 424/195.1, 196.1, DIG. 10;
514/456, 692, 724, 763, 731, 755, 766, 919;
260/350 R

[56] References Cited

FOREIGN PATENT DOCUMENTS 63-104905  5/1988  Japan .
63-159302  7/1988  Japan .
63-264510 11/1988  Japan .
3-52805    3/1991  Japan .

OTHER PUBLICATIONS

The Merck Index, #7242, 9th ed. 1976.
Chem. Pharm. Bull. 40(5) 1130 (1992), Mohammad Ahad Ali et al. "Synthesis and Nematocidal Activity of Hydroxystilbenes".
Chemical Abstracts 78, 48 (1973) 155087t; Gibbs, J. N.
Chemical Abstract 88, 134 (1978) 16230w; Gorham, John.
Chemical Abstracts 111, 434 (1989) 171162u, Koichiro et al.

Primary Examiner—John W. Rollins
Attorney, Agent, or Firm—David G. Conlin; George W. Neuner

[57] ABSTRACT

Disclosed are (1) pest control chemicals against the pine wood nematodes containing an extract from a pine tree with an organic solvent, (2) a repellent against the pine wood nematodes containing α-humulene or a mixture of α-humulene and β-bisabolene, (3) a repellent against the pine wood nematodes containing a mixture of α-pinene and calarene, (4) a nematicide against the pine wood nematodes containing methyl ferulate, (+)-pinoresinol or a mixture thereof, and (5) highly effective pest control chemicals against pine wood nematodes containing hydroxystilbenes or salts thereof which are prepared by synthesizing methoxystilbenes from benzyl phosphonates and methoxybenzaldehydes by a Wittig-Horner reaction, performing demethylation to obtain the hydroxystilbenes, and preparing the salts thereof by conventional methods if necessary.

9 Claims, 3 Drawing Sheets

PEST CONTROL CHEMICALS AGAINST PINE WOOD NEMATODES

BACKGROUND OF THE INVENTION

The present invention relates to a pest control chemical for controlling pine wood nematodes (*Bursaohelenchus xylophilus* Mamiya and Kiyohara), and particularly to a repellent and a nematicide against the pine wood nematodes comprising a substance contained in pine trees such as Formosan masson pines (*Pinus massoniana* Lamb), Eastern white pines (*Pinus strobus* L.) and Longleaf pines (*Pinus palustris* Mill.), to a nematicide against pine wood nematodes containing a hydroxystilbene, and to a method for synthesizing hydroxystilbenes.

As well known, the pine wood nematode, fungivorous nematode, enters pine wood tissues and propagate to cause the pine trees to die.

The mechanism by which the pine wood nematodes cause the pine trees to die is considered as follows:
a) In the pine trees infected with the pine wood nematodes are produced toxins (phytoalexins) such as benzoic acid (1), catechol (2), dihydroconiferyl alcohol (3), 8-hydroxycarvotanacetone (4) and 10-hydroxyverbenone (5),
b) The nematodes secrete cellulase,
c) Tracheids of the pine trees are clogged with $\alpha$-pinene and $\beta$-pinene abnormally accumulated after the nematode infection, and
d) Toxins are secreted by molds which propagate in the pine trees after the nematode infection.

The pine wood nematodes are transmitted to the pine trees through injurious insects such as a pine sawyer (*Monochamus alternatus* Hope).

Previous methods for preventing pine trees from dying by the pine wood nematodes mainly include (1) Cutting down damaged trees to exterminate ova, pupae and adults present in the damaged trees before the pine sawyers carrying nematodes, which are directly responsible for the death of the pine trees, escape from the damaged trees, and (2) the insecticide applications (sprinkling and cropdusting) for preventing maturing feeding after eclosion and escape of the pine sawyers. The insecticides used herein include organic phosphorus pesticides, NAC agents (1-naphthyl-N-methylcarbamate), PAP agents (ethyl dimethyl-dithiophosphorylphenylacetate), EDB agents (1,2-dibromoethyl), MPP agents (0,0-dimethyl-0-[3-methyl-4-(methylthio)-phenyl]thiophosphate) and MEP agents (dimethyl(3-methyl-4-nitrophenyl) thiophosphate).

In addition to the above-mentioned insecticides for the pine sawyers, nematicides for directly exterminating the pine wood nematodes in pine trees include a levamisole hydrochloride agent containing levamisole hydrochloride as a main insecticidal ingredient (trade name: "Century", Mitsubishi Petrochemical Co. LTD., Japan), a mesulfenfos agent (trade name: "Nemanon", Nihon Bayer Agro Chem. K/K, Japan) and a morantel tartarate agent (trade name: "Greenguard", Fizer Pharmaceutical INC., Japan).

The previous methods for exterminating the pine sawyers have the following problems:
(1) A great deal of labor is required.
(2) It is difficult to decide the suitable time of insecticide application because the time of eclosion and escape of the pine sawyers differs from year to year.
(3) The effectiveness of the insecticides has become lowered.
(4) In order to achieve the exterminating effect in forests and fields, the dosage per unit area is required to be 10 times that generally used in agriculture.
(5) Social problems such as the remaining of the given insecticides in soil, the remaining in water systems and the effect on ecosystems such as surrounding animals and plants are encountered.

The sufficient controlling effect can not be attained because of these problems.
(6) The previous synthetic nematicides for directly exterminating the pine wood nematodes in wood are effective, but have a problem in safety because of their toxicity.

It has hitherto been unknown at all that an extract from a pine tree with an organic solvent, an extracted compound or hydroxystilbenes is effective as a pest control chemical for controlling the pine wood nematodes.

SUMMARY OF THE INVENTION

As a result of intensive studies on the extermination of the pine wood nematodes, the present inventor discovered that Formosan masson pine, Eastern white pine and Longleaf pines contained substances having repellent activity and nematicidal activity against the pine wood nematodes, that the substances had no problem in their safety, and hydroxystilbenes had nematicidal activity against the pine wood nematodes, thus completing the present invention.

The present invention provides (1) a pest control chemical against the pine wood nematodes containing an extract from a pine tree with an organic solvent, (2) a repellent against the pine wood nematodescontaining $\alpha$-humulene or a mixture of $\alpha$-humulene and $\beta$-bisabolene, (3) a repellent against the pine wood nematodescontaining a mixture of $\alpha$-pinene and calarene, (4) a nematicide against the pine wood nematodes containing methyl ferulate, (+)-pinoresinol or a mixture thereof, (5) a nematicide against the pine wood nematodes containing a hydroxystilbene or a salt thereof. and (6) a method for preparing a hydroxystilbene or a salt thereof comprising sythesizing a methoxysilbene from a benzyl phosphonate and a methoxybenzaldehyde by a Wittig-Horner reaction, performing demethylation to obtain the hydrxystilbene, and preparing the salt thereof by a conventional method if necessary.

DESCRIPTION OF THE PREFERRED EMBODIMENTS

Organic solvents used for extracting active constituents from pine trees include alcohols such as methyl alcohol, ethyl alcohol, butanol; esters such as ethyl acetate, methyl acetate; hydrocarbons such as pentane, hexane, heptane; hydrocarbon halides such as chloroform, dichloromethane, aromatic hydrocarbons such as benzene, xylene, ethers such as ethyl ether, methyl ether, methyl ethyl ether and ketones such as acetone, methyl ethyl ketone.

Figure 1:
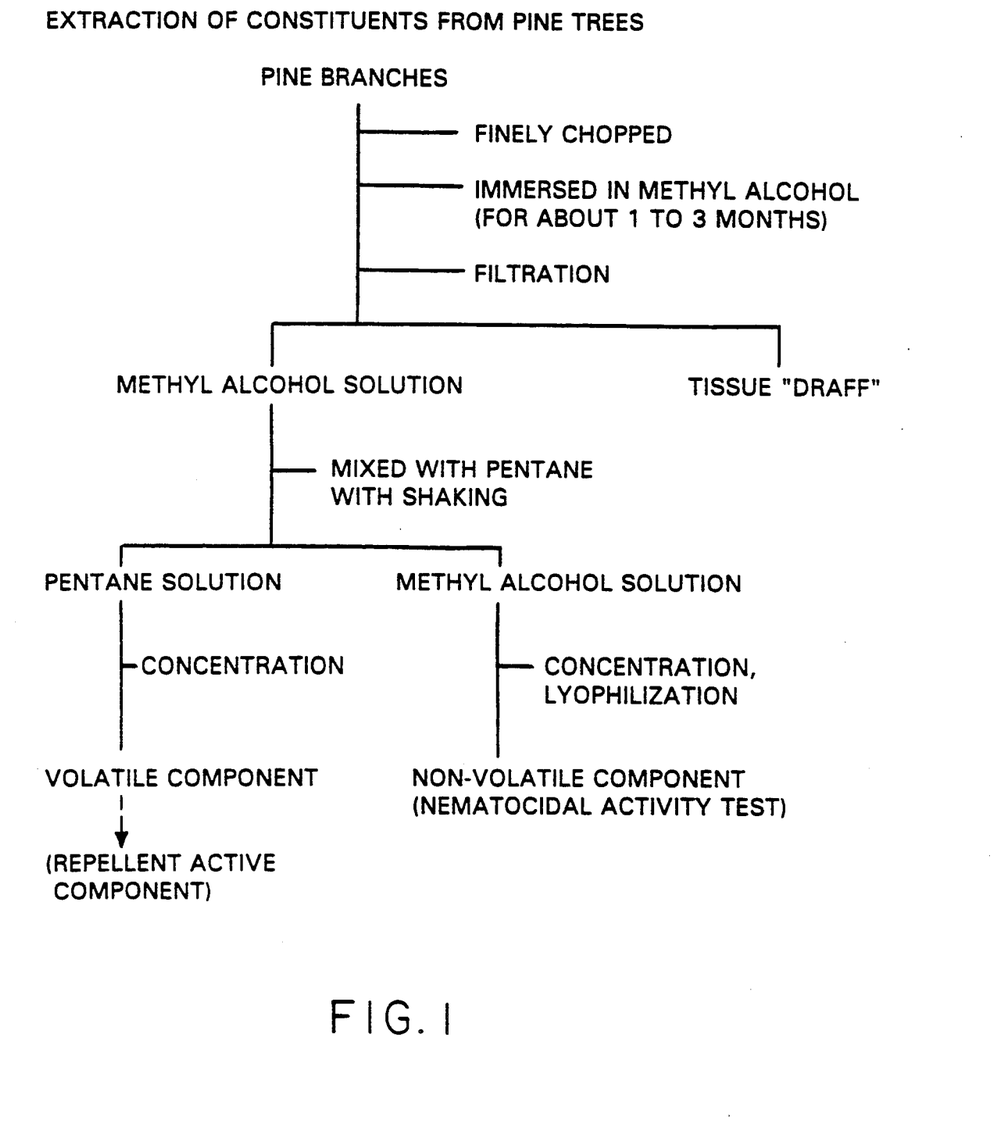
FIG. 1 is a flow chart showing the process of extracting an active ingredient from a pine tree.

The active ingredients are extracted with the organic solvents from the pine trees by the method shown in FIG. 1. The branches of the pine tree are finely chopped, and immersed in methyl alcohol at room temperature to 55° C. for about 1 to 3 months, followed by filtration The methyl alcohol solution thus obtained is mixed with pentane with shaking, and a methyl alcohol layer is separated from a pentane fraction. This methyl alcohol solution is concentrated and lyophilized to give a non-volatile component. The resulting non-volatile component is a viscous brown cake having a woody odor. On the other hand, the pentane solution is concentrated to obtain a volatile component. This volatile component is a brown oil and has an optical rotation $[\alpha]_D^{25} -6.0°$ (c 5.9, $CHCl_3$). The above-non-volatile component is further treated as described below.

Next, for the non-volatile component, the nematicidal activity against the pine wood nematodes and the resistancy of the pines examined trees against the pine wood nematodes are given in Table 1.

The nematicidal activity test was conducted according to the following method:

1) About 300 propagative pine wood nematodes incubated on the colony of *Botorytis cinerea* were placed in a plastic petri dish for counting (having a diameter of 5.5 cm).
2) The samples were dissolved in 2% ethanol solutions to concentrations 1,000 ppm, 100 ppm and 10 ppm, respectively, to prepare test solutions.
3) 4 ml of each test solution was poured into the above-mentioned petri dish in which the nematodes were placed. As a control solution, a 2% ethanol solution in which the sample was not dissolved was used.
4) The test solutions were allowed to stand at 10° C. in the dark, and the number of the moving nematodes was counted under a stereoscopic microscope every 24 hours for 3 days, thereby determining the survival rate. For each of the solutions, the test was repeated 5 times under the same conditions, and the mean value was determined therefrom to take it as the mean survival rate. In this case, the mean survival rate of the nematodes in the control test solution was 99.5% and the standard error thereof was ±3% at any time.
5) The nematicidal activity was indicated by the relative lethal rate. The relative lethal rate was determined by the following equation:

$$\text{Relative lethal rate (\%)} = 100 - \frac{\text{Mean survival rate in sample solution}}{\text{Mean survival rate in control solution}} \times 100$$

For the resistance to the pine wood nematodes, the data described in *Shinrin Byochu-jugai Bojo-gijutsu*, page 321 (1981) (published by Forest Protection Society of Japan) were used.

TABLE 1

Nematicidal activity of the non-volatile components contained in pines (branches) and the resistancy of the pine trees against the pine wood nematodes

| Pine | Relative lethal rate (%) (1000 ppm) After 1 day | Grade of resistance |
|---|---|---|
| Eastern white pine | 54.1 | Highly resitant |
| Longleaf pine | 45.1 | Highly resistant |
| Shortleaf pine | 38.3 | Resistant |
| Loblolly pine | 37.0 | Highy resistant |
| Formosan masson pine | 36.8 | Resistant |
| *Pinus elliottii* L. | 34.4 | Resistant |
| Pitch pine (*Pinus rigida* Mill.) | 27.2 | Resistant |
| European red pine | 6.3 | Highly susceptible |
| Japanese red pine | 0.0 | Susceptible |
| Japanese black pine | 0.0 | Highly susceptible |

(The data of the resistance shown in Table 1 were cited from Shinrin Byochu-jugai Bojo-gijutsu, described by Forest Protection Society of Japan.)

From the results shown in Table 1, it is clear that the Eastern white pin, Longleaf pine, Formosan masson pine, Shortleaf pine (*Pinus echinata* Mill.), Loblolly pine (*Pinus taeda* L.) and *Pinus elliottii* L. pine trees contain substances having nematicidal activity against the pine wood nematodes.

Figure 2:
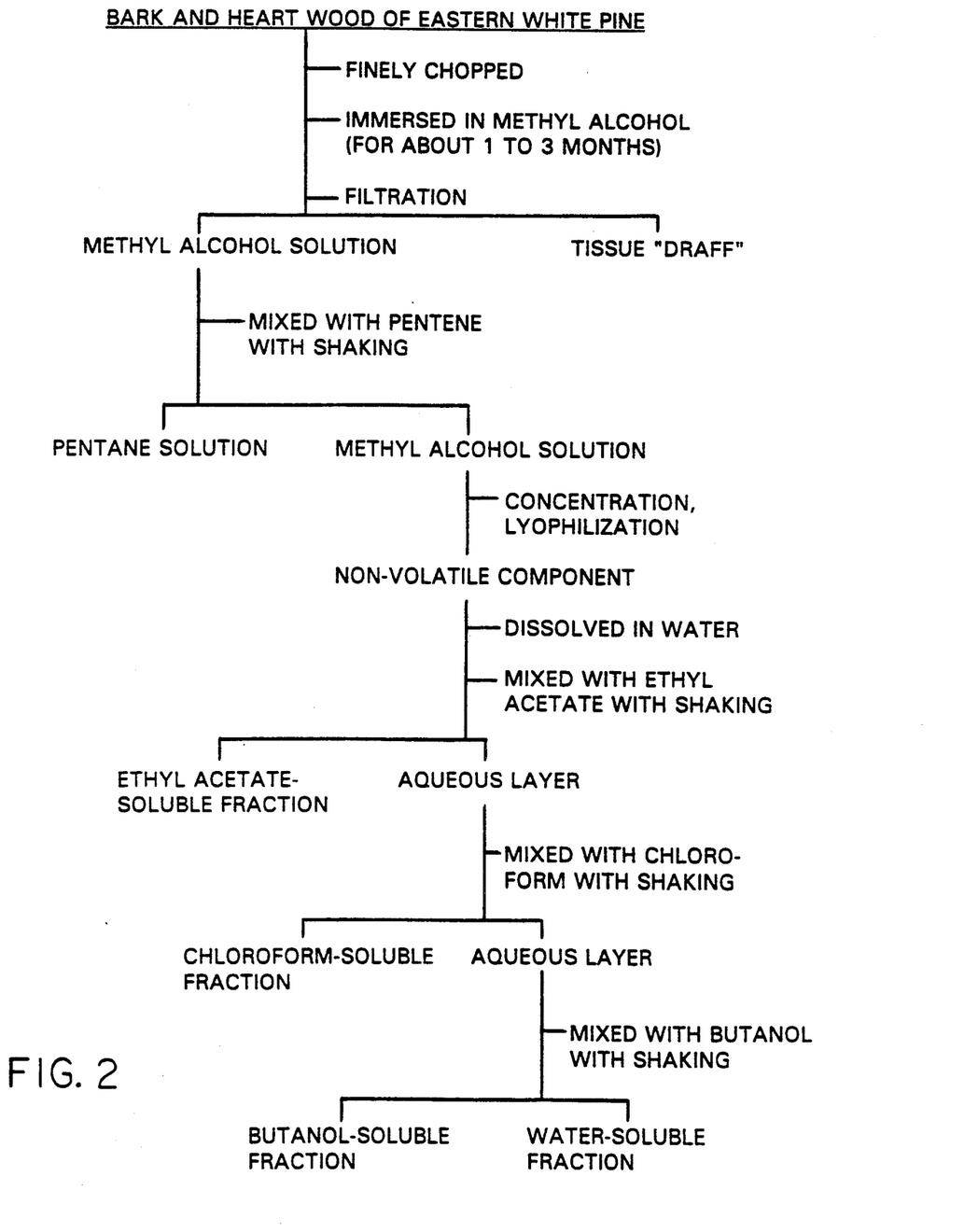
FIG. 2 is a flow chart showing the process of extracting a substance which has a nematicidal activity against the pine wood nematodes from an Eastern white pine.

Then, the above-mentioned non-volatile component obtained from the bark and heart wood of Eastern white pines was further treated according to the process shown in FIG. 2 to give four kinds of fractions. For these fractions, the nematicidal activity against the pine wood nematodes was tested. The test was conducted according to the above-mentioned method. Results thereof are given in Table 2. The results reveal that a nematicide is contained in the heart wood of the pine trees.

Further, they reveal that the nematicide is contained in a chloroform soluble fraction, an ethyl acetate-soluble fraction and a butanol-soluble fraction.

TABLE 2

Nematicidal activity against the pine wood nematodes of the four kinds of fractions obtained from the bark and the heart wood of Eastern white pine trees

| | Relative lethal rate (%) (1000 ppm) | |
|---|---|---|
| Fraction | Bark (1.3 kg) | Heart wood (11.2 kg) |
| Ethyl acetate-soluble fraction | 56.6 (8.2 g) | 99.8 (82.1 g) |
| Chloroform-soluble fraction | 0.0 (28.5 g) | 100 (10.1 g) |
| Butanol-soluble fraction | 62.1 (24.1 g) | 94.5 (17.3 g) |
| Water-soluble fraction | 0.0 (28.4 g) | 0.0 (36.5 g) |

Figure 3:
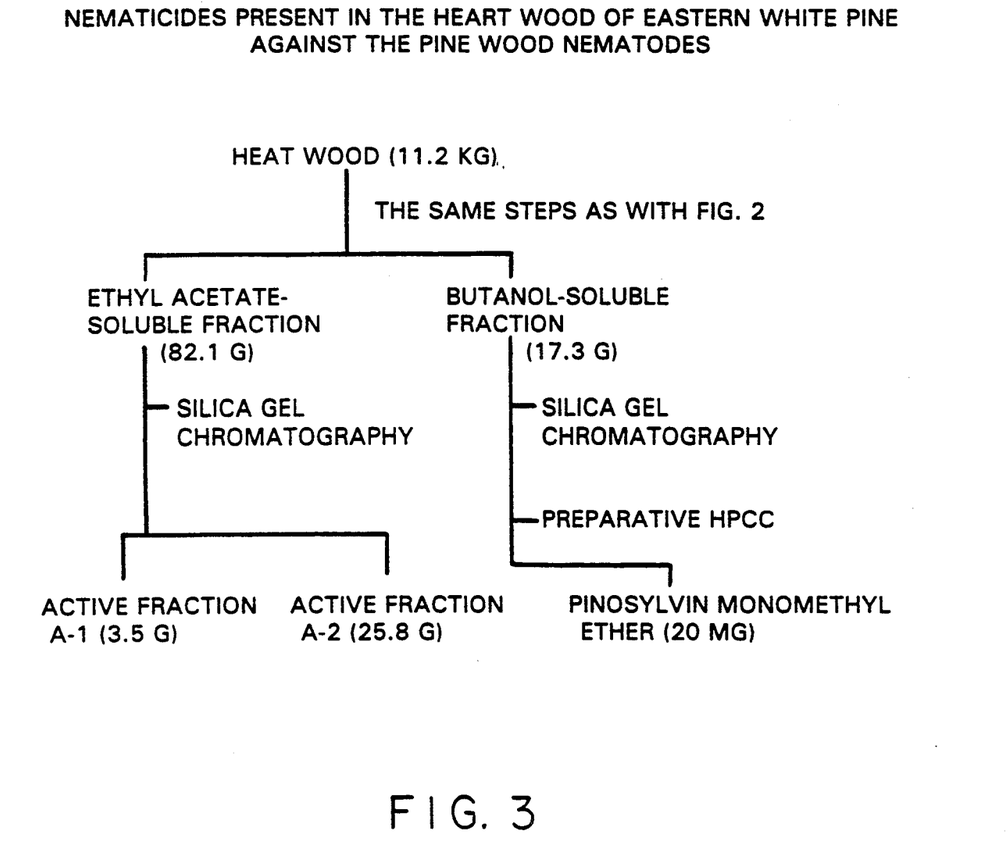
FIG. 3 is a flow chart showing the process of extracting a substance which has a nematicidal activity against the pine wood nematodes and occurs in the heart wood of an Eastern white pine.

Subsequently, the heart wood of Eastern white pines was treated according to the process shown in FIG. 3 to obtain an ethyl acetate-soluble fraction and a butanol-soluble fraction. Then, the ethyl acetate-soluble fraction was subjected to silica gel chromatography to give two active fractions A-1 and A-2. On the other hand, the butanol-soluble fraction was subjected to gel filtration chromatography, silica gel chromatography, and subsequently preparative high performance liquid chromatography, thereby obtaining pinosylvin monomethyl ether represented by the following formula:

Pinosylvin monomethyl ether

For methyl ferulate, (+)-pinoresinol and pinosylvin monomethyl ether of the present invention obtained from Formosan masson pines according to the method described below, and for an agricultural chemical, "Century" (trade name Mitsubishi Petrochemical Co., LTD., Japan), the nematicidal activity was tested. The test was conducted as described above. Results thereof are shown in Table 3.

TABLE 3

Substances having nematicidal activity against the pine wood nematodes obtained from Eastern white pine and Formosan masson pines

| | Concentration (ppm) | Relative lethal rate (%) | | |
|---|---|---|---|---|
| | | After 1 day | After 2 days | After 3 days |
| Eastern white pine | | | | |
| A-1 | 100 | 43.8 | 49.1 | |
| A-2 | 100 | 41.5 | 57.8 | |
| Formosan masson pine | | | | |
| Methyl ferulate | 100 | 20.6 | 45.5 | 82.7 |
| (+)-Pinoresinol | 100 | 23.0 | 46.9 | 62.7 |
| Pinosylvin monomethyl ether | 10 | 100 | 100 | — |
| | 5 | 32.7 | 35.5 | |
| | 4 | 26.6 | 28.6 | |
| Agricultural chemical, "Century" | 100 | 88.5 | 89.4 | 91.6 |
| | 10 | 41.9 | 51.7 | 54.1 | the nematicidal activity of pinosylvin monomethyl ether and its derivatives similar thereto in structure is as given in Table 4.

TABLE 4

| Structure | Concentration (ppm) | Relative lethal rate (%) | |
|---|---|---|---|
| | | After 1 day | After 2 days |
| Natural product | 10 | 100 | 100 |
| | 5 | 32.7 | 35.5 |
| Synthetic product | 10 | 100 | 100 |
| | 5 | 86.9 | 87.8 |
| | 4 | 48.0 | 49.0 |
| (OMe, OMe) | 100 | 5.2 | 14.1 |
| | 50 | 1.2 | 3.5 |
| (OH, OH) | 100 | 100 | 100 |
| | 50 | 67.5 | 68.8 |
| | 10 | 11.6 | 12.0 |
| cis (OMe, OMe) | 100 | 56.3 | 56.3 |
| | 50 | 44.7 | 43.5 |
| cis (OH, OMe) | 50 | 100 | 100 |
| | 10 | 10.5 | 9.1 |
| | 5 | 5.6 | 4.4 |
| cis (OH, OH) | 100 | 0 | 0.5 |
| saturated (OH, OMe) | 100 | 100 | 100 |
| | 50 | 48.7 | 48.3 |

In the pest control chemicals for controlling pine wood nematodes which contain these extracts, the content of the extract ingredients is 1 to 2%, and the extract ingredients are used in combination with other known carriers.

α-Humulene, one of the repellent ingredients of the present invention, presents in the heart wood of Formosan masson pines, and is obtained by extracting the heart wood of Formosan masson pines with organic solvents such as alcohols, esters, hydrocarbons, hydrocarbon halides, aromatic hydrocarbons, ethers and ketones.

α-Humulene thus obtained has a repellent activity against dispersal pine wood nematodes (4th stage) as given in Table 5.

The method for testing the repellent activity will be described below.

The repellents of the present invention contain α-humulene in an amount of 1 to 2%, in combination with other known carriers.

Compositions containing α-humulene and β-bisabolene can enhance repellent activity. Although the content of β-bisabolene is not limited, it is preferably about 30 to 50% based on α-humulene.

Of terpene hydrocarbons other than α-humulene, hydrocarbons having repellent activity against the pine wood nematodes include α-pinene, β-bulnesene and calarene.

Furthermore, a mixture of the terpene hydrocarbons exhibiting repellent activity against the pine wood nematodes is obtained, for example, by the following method.

Heart wood (13 kg) of Formosan masson pines is treated according to the method shown in FIG. 1 to give a volatile component (14 g). The volatile component is repeatedly subjected to silica gel chromatography to give a mixture I (1.1 g) [α-humulene (60%)+β-bisabolene (40%)] and a mixture II (1.5 g) [α-pinene (60%)+calarene (40%)], each of which is a mixture of two kinds of terpene hydrocarbons exhibiting repellent activity against the pine wood nematodes.

These compounds are represented by the following formulae:

The repellent activity against the pine wood nematodes was tested for these terpene hydrocarbons as shown below.

The method for testing attractiing activity against the pine wood nematodes (T-tube method) [M. Ishikawa, Y. Shuto, and H. Watanabe, *Agric. Biol. Chem.*, 50, 1863 (1986)] was partially modified to test the repellent activity test against the pine wood nematodes (Tables 4 and 5).

Namely, in the Watanabe method, a sample is allowed to be adsorbed on a boiling stone, and air is blown to the surface of the boiling stone, thereby diffusing vapor of the sample. In contrast, in the present invention, a sample was previously dissolved in an aqueous solution of a surface active agent (0.1% Triton X-100), and air purified through an active carbon filter was blown into the solution, thereby diffusing vapor of the sample. This made it possible to conduct the activity test for a long time of 18 hours (3 hours in the case of the Watanabe method), whereby more reproducible data could be obtained. The dispersal pine wood nematodes were obtained by separation from pine sawyers which grew wings and escaped from pine trees from June to August. The propagative pine wood nematodes (all stages) were the same as those used in the nematicidal activity test described above.

Results thereof are given in Tables 5 and 6.

TABLE 5

Repellent activity of α-humulene against the pine wood nematodes

| | Repellent index | |
|---|---|---|
| | Dispersal nematodes | Propagative nematodes |
| α-Humulene | 26.7 ± 5.8 | 10.5 ± 4.6 |

$$\text{Repellent index} = \frac{\text{Number of nematodes on the control side} - \text{Number of nematodes on the sample side}}{\text{Number of nematodes on the control side} + \text{Number of nematodes on the sample side}} \times 100$$

The repellent activity test was conducted by the T-tube method.

The test was repeated at least 5 times.

TABLE 6

Repellent activity of terpene hydrocarbon mixtures against the dispersal nematodes

| Mixture | Repellent activity |
|---|---|
| (A) α-Humulene (60%) β-Bisabolene (40%) | +47.1 ± 19.3 |
| (B) α-Pinene (60%) Calarene (40%) | +44.5 ± 18.4 |

A stronger repellent activity appeared by adding β-bisabolene to α-humulene.

Methyl ferulate and (+)-pinoresinol having a nematicidal activity against the propagative pine wood nematodes, are represented by the following formulae, and are contained in the outer bark of Formosan mason pines.

Methyl ferulate (+)-Pinoresinol

These compounds are obtained by treating the bark of Formosan masson pines in a manner similar to that described above, using the same organic solvent, for separation and extraction.

Methyl ferulate is also prepared by methylating a commercial ferulic acid with diazomethane.

For these compounds, the nematicidal activity against the propagative pine wood nematodes was tested. The test method was the same as described above.

Results thereof are given in Tables 7 and 8.

TABLE 7

Nematicidal activity against the propagative pine wood nematodes

| | Relative lethal rate (%) (100 ppm) | | |
|---|---|---|---|
| | After 1 day | After 2 days | After 3 days |
| Methyl ferulate | 20.6 | 45.5 | 82.7 |
| (±)-Pinoresinol | 23.0 | 46.9 | 62.7 |
| Agricultural chemical, "Century" | 88.5 | 89.4 | 91.6 |

$$\text{Relative lethal rate (\%)} = 100 - \frac{\text{Survival rate of nematodes in sample solution}}{\text{Survival rate of nematodes in control solution}} \times 100$$

TABLE 8

Nematicidal activity of methyl ferulate and its six derivatives against the propagative pine wood nematodes

| Structure | Relative lethal rate (%) (100 ppm) | | |
|---|---|---|---|
| | After 1 day | After 2 days | After 3 days |
| HO-C₆H₃(OCH₃)-CH=CH-COOCH₃ | 38.2 | 51.2 | 82.7 |
| HO-C₆H₃(OCH₃)-CH₂-CH₂-COOCH₃ | 35.4 | 50.5 | 61.0 |
| HO-C₆H₃(OCH₃)-CH=CH-COOH | 29.6 | 34.9 | 43.8 |
| HO-C₆H₃(OCH₃)-CH=CH-COONa | 12.3 | 14.2 | 6.3 |
| HO-C₆H₃(OCH₃)-CH=CH-COOK | 2.2 | 10.1 | 19.5 |
| HO-C₆H₃(OCH₃)-CH=CH-CH₂OH | 8.2 | 18.0 | 23.2 |
| HO-C₆H₃(OCH₃)-CH₂-CH₂-CH₂OH | 6.6 | 5.7 | 15.1 |

Further, the nematicidal activity against the pine wood nematodes was examined for monohydroxystilbenes and salts thereof shown in Table 9. Results thereof are shown in Table 10. From these results, the present inventors discovered that monohydroxystilbenes similar to pinosylvin monomethyl ether had a stronger nematicidal activity than pinosylvin monomethyl ether.

This nematicidal activity test was conducted in the following manner. Purely subcultured propagative pine wood nematodes of the Shimabara species were used for this nematicidal activity test.

First, the nematodes were placed in a petri dish for counting, and the number of the moving nematodes was counted under a stereoscopic microscope.

Then, each of the test solutions was poured into the petri dish, followed by standing at 10° C. in the dark. The test solutions were used at concentrations of 100 ppm, 50 ppm, 10 ppm, 5 ppm, 2 ppm, 1 ppm and 0.5 ppm.

The number of the moving nematodes was counted again after 1 day and 2 days.

Taking the nematodes which did not move as died, the ratio of the number of the nematodes which had lived first to that of the nematodes which died was calculated as the lethal rate.

As a control solution for comparison to confirm whether or not the nematodes were really killed by the samples, a 1% ethanol solution was used.

TABLE 9

| Sample No. | Structural formula | Name of substance |
|---|---|---|
| 1 | [stilbene with OH and OMe] | Pinosylvin monomethyl ether |
| 2 | [stilbene with two OMe] | Pinosylvin dimethyl ether |
| 3 | [stilbene with two OH] | Pinosylvin |
| 4 | [cis-stilbene with two OMe] | Cis-3,5-dimethoxystilbene |

TABLE 9-continued

| Sample No. | Structural formula | Name of substance |
|---|---|---|
| 5 | | Cis-3-hydroxy-5-methoxy-stilbene |
| 6 | | Cis-3,5-di-hydroxy-stilbene |
| 7 | | 7,7'-Dihydro-3-hydroxy-5-methoxy-stilbene |
| 8 | | 2-Methoxy-stilbene |
| 9 | | 2-Hydroxy-stilbene |
| 10 | | 3-Methoxy-stilbene |
| 11 | | 3-Hydroxy-stilbene |
| 12 | | 4-Methoxy-stilbene |
| 13 | | 4-Hydroxy-stilbene |
| 14 | | 2,2'-Dimethoxy-stilbene |
| 15 | | 2-Hydroxy-2'-methoxy-stilbene |
| 16 | | 2,2'-Dihydroxy-stilbene |
| 17 | | 2,3'-Dimethoxy-stilbene |
| 18 | | 3-Hydroxy-2'-methoxy-stilbene |
| 19 | | 2-Hydroxy-3'-methoxy-stilbene |
| 20 | | 2,3'-Dihydroxy-stilbene |
| 21 | | 2,4'-Dimethoxy-stilbene |
| 22* | | 2-Hydroxy-4'-methoxy-stilbene |

TABLE 9-continued

| Sample No. | Name of substance |
|---|---|
| 23 | 4-Hydroxy-2'-methoxystilbene |
| 24 | 2,4'-Dihydroxystilbene |
| 25 | 3,3'-Dimethoxystilbene |
| 26 | 3-Hydroxy-3'-methoxystilbene |
| 27 | 3,3'-Dihydroxystilbene |
| 28 | Pinosylvin monomethyl ether sodium salt |
| 29 | Pinosylvin monomethyl ether potassium salt |
| 30 | 2-Hydroxystilbene sodium salt |
| 31 | 2-Hydroxystilbene potassium salt |
| 32 | 3-Hydroxystilbene sodium salt |
| 33 | 3-Hydroxystilbene potassium salt |
| 34 | 4-Hydroxystilbene sodium salt |
| 35 | 4-Hydroxystilbene potassium salt |
| 36 | 2-Propenylphenol |
| 37 | 4-Propenylphenol |
| 38 | 4-Propenylanisole |
| 39 | 4-Methoxystyrene |
| 40 | 2-Allylphenol |
| 41 | Isoeugenol |
| 42 | Phenol |

TABLE 9-continued

| Sample No. | Structural formula | Name of substance |
| --- | --- | --- |
| 43 | [structure] | o-Cresol |
| 44 | [structure] | m-Cresol |
| 45 | [structure] | p-Cresol |
| 46 | [structure] | Thymol |
| 47 | [structure] | Carvacrol |
| 48 | [structure] —COOH | Benzoic acid |

TABLE 10

| Sample No. | Nematode lethal rate (%) (after 2 days) | | | | | | |
| --- | --- | --- | --- | --- | --- | --- | --- |
| | 100 (ppm) | 50 (ppm) | 10 (ppm) | 5 (ppm) | 2 (ppm) | 1 (ppm) | 0.5 (ppm) |
| 1 | 100 | 100 | 100 | 88 | 11 | — | — |
| 2 | 14 | 4 | — | — | — | — | — |
| 3 | 100 | 69 | 12 | — | — | — | — |
| 4 | 56 | 44 | — | — | — | — | — |
| 5 | 100 | 100 | 9 | 4 | — | — | — |
| 6 | 1 | — | — | — | — | — | — |
| 7 | 100 | 48 | — | — | — | — | — |
| 8 | 0 | — | — | — | — | — | — |
| 9 | 100 | 100 | 100 | 99 | 80 | 61 | 0.5 |
| 10 | 98 | 99 | — | — | — | — | — |
| 11 | 100 | 100 | 100 | 100 | 97 | 9 | — |
| 12 | 30 | — | — | — | — | — | — |
| 13 | 100 | 100 | 92 | 95 | 83 | 44 | 34 |
| 14 | 20 | — | — | — | — | — | — |
| 15 | 100 | 100 | 13 | — | — | — | — |
| 16 | 100 | 100 | 0 | — | — | — | — |
| 17 | 41 | — | — | — | — | — | — |
| 18 | — | — | 42 | 19 | 17 | — | — |
| 19 | 100 | 100 | 100 | 64 | 2 | — | — |
| 20 | 100 | 100 | 98 | — | — | — | — |
| 21 | 19 | — | — | — | — | — | — |
| 22* | 100 | 100 | 100 | 100 | 100 | 95 | 45 |
| 23 | — | — | 56 | 16 | — | — | — |
| 24 | 100 | 100 | 49 | — | — | — | — |
| 25 | 56 | — | — | — | — | — | — |
| 26 | 100 | 100 | 100 | 100 | — | 83 | 8 |
| 27 | 100 | 100 | 18 | — | — | — | — |
| 28 | 100 | 100 | 96 | 0 | — | — | — |
| 29 | 100 | 100 | 99 | 18 | — | — | — |
| 30 | 100 | 100 | 100 | 100 | 71 | — | — |
| 31 | 100 | 100 | 100 | 100 | 48 | — | — |
| 32 | 100 | 100 | 100 | 100 | 61 | — | — |
| 33 | 100 | 100 | 100 | 100 | 52 | — | — |
| 34 | 100 | 100 | 100 | 100 | 44 | — | — |
| 35 | 100 | 100 | 100 | 100 | 60 | — | — |
| 36 | 94 | 1 | — | — | — | — | — |
| 37 | 99 | 6 | — | — | — | — | — |
| 38 | 63 | 0 | — | — | — | — | — |
| 39 | 1 | — | — | — | — | — | — |
| 40 | 3 | — | — | — | — | — | — |
| 41 | 0 | — | — | — | — | — | — |
| 42 | 0 | — | — | — | — | — | — |
| 43 | 0 | — | — | — | — | — | — |
| 44 | 1 | — | — | — | — | — | — |
| 45 | 0 | — | — | — | — | — | — |
| 46 | 2 | — | — | — | — | — | — |
| 47 | 1 | — | — | — | — | — | — |
| 48 | 0 | — | — | — | — | — | — |

*This sample showed a nematode lethal rate of 0.2% at a concentration of 0.25 ppm.

Of these, particularly excellent are 3-hydroxystilbene (sample No. 11), 3-hydroxystilbene sodium salt (sample No. 32), 3-hydroxystilbene potassium salt (sample No. 33), 2-hydroxystilbene (sample No. 9), 2-hydroxystilbene sodium salt (sample No. 30), 2-hydroxystilbene potassium salt (sample No. 31), 4-hydroxystilbene (sample No. 13), 4-hydroxystilbene sodium salt (sample No. 34), 4-hydroxystilbene potassium salt (sample No. 35), 2-hydroxy-3'-methoxystilbene (sample No. 19), 2-hydroxy-4'-methoxystilbene (sample No. 22) and 3-hydroxy-3'-methoxystilbene (sample No. 26).

The hydroxystilbenes are synthesized by the following method:

Synthesis of Hydroxystilbenes

Methoxystilbenes (C) were synthesized from benzyl phosphonates (A) and methoxybenzaldehydes (B) by the Wittig-Horner reaction, and then, demethylation was carried out using pyridinium chloride or boron tribromide to obtain hydroxystilbenes (D).

A: As the benzyl phosphonate compounds (A), raw materials for the Wittig-Horner reaction, a-0, a-2 and a-3 were used.

Of these, as a-0, a commercially available product was used, but a-2 and a-3 were synthesized in the following manner:

(Yield 100%)

B: As the methoxybenzaldehydes (B), the other raw materials for the Wittig-Horner reaction, b-2, b-3 and b-4 were used, all of which were commercially available products.

(b-2)   (b-3)   (b-4)

C: The following methoxystilbenes were obtained by the Wittig-Horner reaction:

(c-0.2)
(Sample No. 8)

(c-0.3)
(Sample No. 10)

(c-0.4)
(Sample No. 12)

(c-2.3)
(Sample No. 17)

(c-2.4)
(Sample No. 21)

(c-3.3)
(Sample No. 25)

D: The methoxystilbenes (C) were subjected to demethylation reaction to obtain the following hydroxystilbenes (D):

(d-0.2)
(Sample No. 9)

(d-0.3)
(Sample No. 11)

(d-0.4)
(Sample No. 13)

(d-2.3)
(Sample No. 19)

-continued (d-2.4)
(Sample No. 22)

(d-3.3)
(Sample No. 26)

These compounds showed a very strong nematicidal activity.

In demethylation reaction, Lewis acid can be used, such as the acid pyridinium chloride or boron tribromide was used as process 1 or process 2.

The nematicides containing these compounds having the nematicidal activity as main ingredients contain these active ingredients in an amount of about 1 to 10%, in combination with other known carriers, etc.

As the carriers of the pest control chemicals including the repellents and the nematicides for the pine wood nematodes, liquid carriers or solid carriers are used depending on the purpose of their use.

The liquid carriers include water, alcohols, ketones, ethers, aromatic hydrocarbons, acid amides and esters. The solid carriers include known solid carriers such as mineral powders, alumina, sulfur powder and active carbon.

For the formulation, the pest control chemicals can be used as injection and cataplasm. These preparations may contain emulsifiers, suspensions, stabilizers, stickers, penetrants and dispersing agents, if necessary, and can be prepared by methods known in the art.

The extracts from the pine trees with the organic solvents have the activity of controlling the pine wood nematodes. α-Humulene obtained from the pine trees or synthesized, the mixture of α-humulene and β-bisabolene, and the mixture of α-pinene and calarene have the repellent activity against the pine wood nematodes. Further, methyl ferulate, (+)-pinoresinol and hydroxystilbenes including pinosylvin monomethyl ether have the nematicidal activity against the pine wood nematodes.

The following example is given by way of illustration and is not to be construed as a limitation of the invention.

1. Preparation of Extracts Having the Activity of Controlling the Pine Wood Nematodes 1) Preparation of Substances Having the Activity of Controlling the Pine Wood Nematodes from the Branches of Eastern White Pines (1) The branches (570 g) of Eastern white pines were finely chopped, and immersed in 3 liter of methyl alcohol at room temperature for 3 months, followed by filtration to obtain 3 liter of a methyl alcohol solution. Then, 0.6 liter of pentane was added to the methyl alcohol solution, and mixed in a separating funnel with shaking for 30 minutes. Then, 0.5 liter of a pentane solution was separated from 3.1 liter of a methyl alcohol solution. The pentane solution was concentrated to give 5 g of a volatile component. The resulting volatile component was a brown oil, and had an optical rotation $[\alpha]_D^{25}$ of $-6.0°$ (c 5.9, $CHCl_3$). On the other hand, the methyl alcohol solution after removal of the pentane solution was concentrated and lyophilized to give a non-volatile component. This non-volatile component was a viscous brown cake (FIG. 1).

(2) 8 g of the above-mentioned non-volatile component dissolved in 0.3 liter of water, and a) 0.6 liter of ethyl acetate was added thereto, followed by mixing in a separating funnel with shaking to give 0.5 liter of an ethyl acetate-soluble fraction, from which 0.746 g of a viscous brown cake was obtained. Subsequently, b) 0.6 liter of chloroform was added to the aqueous layer after removal of the ethyl acetate extract, followed by mixing similarly with shaking for 30 minutes to give 0.5 liter of a chloroform-soluble fraction, from which 0.036 g of a viscous brown cake was obtained. Further, c) 0.6 liter of butanol was added to the aqueous layer, followed by mixing similarly with shaking to obtain 0.5 liter of a butanol-soluble fraction, from which 1.556 g of a viscous brown cake was obtained (FIG. 2).

Preparation of Substances Having the Activity of Controlling the Pine Wood Nematodes from the Heart Wood of Eastern White Pines The heart wood (11.2 kg) was finely chopped, and immersed in 30 liter of methyl alcohol at room temperature for 3 months, followed by filtration to give 30 liter of a methyl alcohol solution. Then, the resulting solution was treated in the same manner as with the branches (described above) (see FIGS. 2 and 3) to give an ethyl acetate-soluble fraction (82.1 g) and a butanol soluble fraction (17.3 g).

(1) The ethyl acetate-soluble fraction (82.1 g) was further subjected to silica gel chromatography to give two active fractions A-1 (3.5 g) and A-2 (25.8 g).

(2) The butanol-soluble fraction (17.3 g) was subjected to gel filtration chromatography, silica gel chromatography, and subsequently preparative high performance liquid chromatography to obtain pinosylvin monomethyl ether (20 mg).

2. Preparation of Substances Having Repellent Activity Against the Pine Wood Nematodes and Substances Having Nematicidal Activity Against Them (1) Preparation of α-Humulene As α-humulene, a commercial product (made by Tokyo Kasei Kogyo, Japan) was used. A mixture of repellent active terpene hydrocarbons containing α-humulene and calarene was prepared from the heart wood of Formosan masson pines by the following method.

The heart wood (13 kg) of Formosan masson pines was finely chopped and immersed in methyl alcohol (50 liter). After filtration, 18 liter of pentane was added to the resulting methyl alcohol solution (50 liter), followed by mixing with shaking to obtain a pentane solution (16 liter). This pentane solution concentrated to give a volatile component (14 g). The resulting volatile component was subjected to silica gel chromatography to give two mixtures I (1.1 g) and II (1.5 g) of two kinds of terpene hydrocarbons exhibiting repellent activity against the pine wood nematodes.

Gas chromatography and gas chromatograph mass spectrometry revealed that the mixture I contained α-humulene (60%) and β-bisabolene (40%), whereas the mixture II contained α-pinene (60%) and calarene (40%).

(2) Preparation of Methyl Ferulate

Methyl ferulate was prepared by methylating commercial ferulic acid (made by Tokyo Kasei Kogyo Co. LTD., Japan) with diazomethane or methyl alcohol acidified with hydrochloric acid (Fisher Method).

Methyl ferulate was also isolated together with (+)-pinoresinol from the outer bark of Formoson masson pines.

(3) Preparation of Methyl Ferulate and (+)-Pinoresinol from the Outer Bark of Formosan Masson Pines The outer bark (14 kg) of Formosan masson pines was finely chopped, and immersed in methyl alcohol (15 liter) for 3 months. After filtration, the resulting methyl alcohol solution was treated in the same manner as with the Eastern white pines (described above) (FIG. 2) to give a butanol-soluble fraction (29 g). Then, the butanol-soluble fraction was subjected to gel filtration chromatography, silica gel chromatography, and subsequently preparative high performance liquid chromatography to obtain methyl ferulate (6 mg) and (+)-pinoresinol (3 mg).

3. Syntheses of 2-, 3-, and 4-hydroxystilbenes (sample Nos. 9, 11 and 13)

Wittig-Horner Reaction

Five grams (36.8 mmol) of 3-methoxybenzaldehyde (b-3) and 10.1 g (44.1 mmol) of diethylbenzyl phosphonate (a-0) are dissolved in 50 ml of anhydrous N,N-dimethylformamide in an atmosphere of nitrogen. Then, 8.9 ml (45.9 mmol) of a methanol solution containing 28% sodium methoxide is added to this solution with cooling at 0° C. on an ice bath.

The resulting mixture is stirred at 0° C. for 1 hour, and further stirred overnight at room temperature.

Then, 200 ml of water is added to the reaction solution and the aqueous mixture is extracted with three 200 ml portions of ethyl acetate. The ethyl acetate layer containing 3-methoxystilbene (c-0-3) is washed with two 50 ml portions of water, and dried over anhydrous Na$_2$SO$_4$, followed by filtration and concentration under reduced pressure. Methanol-water (1:4 v/v) is added in an amount of 100 ml to the concentrate to dissolve it. When the solution is allowed to stand overnight in a refrigerator, 7.0 g (yield: 90.8%) of 3-methoxystilbene (c-0-3) is obtained as pale yellow crystals.

Demethylation Reaction-Process 1

Sixteen grams (138.5 mmol) of pyridinium chloride is added to 6.9 g (32.9 mmol) of 3-methoxystilbene (c-0-3), and the mixture is stirred at 180° C. for 4 hours. After allowed to cool, the mixture is cooled on an ice bath, and 2M aqueous solution of HCl (about 100 ml) is added thereto until the reaction solution becomes acidic. The resulting solution is extracted with three 200 ml portions of ether, and the ether layer is dried over anhydrous Na$_2$SO$_4$, followed by filtration. When the solvent is removed by distillation under reduced pressure, a brown oily product containing 3-hydroxystilbene (d-0-3) (sample No. 11) is obtained.

This oily product is purified by column chromatography [SiO$_2$: 200 g, hexane-ethyl acetate (9:1 v/v)], and further recrystallized from hexane-ethyl acetate, thereby obtaining 4.9 g (yield: 76.9%) of 3-hydroxystilbene (sample No. 11)

(melting point 117°-118° C.)

In a similar manner, 4-methoxystilbene is synthesized from 4-methoxybenzaldehyde and diethylbenzyl phosphonate, and demethylated to obtain 4-hydroxystilbene (sample No. 13) as white needle crystals (melting point: 185°-186° C.).

2-Hydroxystilbene is synthesized by first synthesizing 2-methoxystilbene similarly from 2-methoxybenzaldehyde and diethylbenzyl phosphonate and then subjecting 2-methoxystilbene to demethylation reaction according to process 2 shown below.

Demethylation Reaction-Process 2

In an atmosphere of nitrogen, 7.75 g (36.9 mmol) of 2-methoxystilbene (c-2) is dissolved in anhydrous dichloromethane. Fourty milliliters of a dichloromethane solution containing 3.2 g (12.9 mmol) of boron tribromide is added dropwise thereto at −78° C. (on a dry ice-acetone bath), followed by stirring overnight at room temperature. The reaction solution is cooled on an ice bath, and a 10% aqueous solution of KOH is added thereto drop by drop to decompose a boron complex formed in the reaction solution. This reaction solution is transferred to a separatory funnel, and 2M HCl is added thereto until the aqueous layer becomes acidic. The resulting solution is extracted with three 200 ml portions of chloroform. The chloroform layer is washed with two 50 ml portions of water and dried over anhydrous Na$_2$SO$_4$, followed by filtration. When the solvent is removed by distillation under reduced pressure, a brown oily product containing 2-hydroxystilbene (d-2) is obtained. This oily product is purified by column chromatography [SiO$_2$: 200 g, hexane-ethyl acetate (9:1 v/v)], and further recrystallized from hexane-ethyl acetate, thereby obtaining 5.05 g (yield: 69.9%) of 2-hydroxystilbene (d-2) (sample No. 9) as white needle crystals (melting point: 138°-139° C.).

2) Preparation of Salts of the Hydroxystilbenes

Salts of 2-, 3-, and 4-hydroxystilbenes (sample Nos. 9, 11 and 13) synthesized as above are prepared according to the following reaction formula:

wherein R1, R2, R3, R1', R2 and R3 are as shown in Table 11.

TABLE 11

| Sample No. | R1 | R2 | R3 | Sample No. | R1' | R2' | R3' |
|---|---|---|---|---|---|---|---|
| 11 | H | OH | H | 32 | H | ONa | H |
| 9 | OH | H | H | 30 | ONa | H | H |
| 13 | H | H | OH | 34 | H | H | ONa |

TABLE 11-continued

| Sample No. | R1 | R2 | R3 | Sample No. | R1' | R2' | R3' |
|---|---|---|---|---|---|---|---|
| 11 | H | OH | H | 33 | H | OK | H |
| 9 | OH | H | H | 31 | OK | H | H |
| 13 | H | H | OH | 35 | H | H | OK |

In a small amount (about 5 ml) of ethanol, 1.120 g (5.71 mmol) of 3-hydroxystilbene is dissolved, and 59.9 ml (5.71 mmol) of a 0.095N aqueous solution of NaOH (titrated with a 0.1N solution of oxalic acid) is added dropwise to this solution. When the resulting solution is lyophilized, 1.276 g (yield: 101.8%) of 3-hydroxystilbene sodium salt (sample No. 32) is obtained as a grayish white powder. The reason why the yield exceeds the equivalent amount is considered to be due to moisture and the like.

Similarly, 2-hydroxystilbene sodium salt (sample No. 30) and 4-hydroxystilbene sodium salt (sample No. 34) are obtained from 2-hydroxystilbene and 4-hydroxystilbene, respectively.

In a similar manner, I.398 g (7.13 mmol) of 4-hydroxystilbene is dissolved in a small amount (about 5 ml) of ethanol, and 64.2 ml of a 0.111M aqueous solution of KOH is added dropwise thereto. Thus, 1.688 g of 4-hydroxystilbene potassium salt (sample No. 35) is obtained as a pale yellow powder.

Similarly, 2-hydroxystilbene potassium salt (sample No. 31) and 3-hydroxystilbene potassium salt (sample No. 33) are obtained as a hygroscopic yellow powder and a white powder from 2-hydroxystilbene and 3-hydroxystilbene, respectively.

3) Synthesis of 2-Hydroxy-4'-Methoxystilbene (Sample No. 22), etc.

Synthesis of a Raw Material, 2-Methoxybenzyl Phosphonate (a-2)

(1) Five milliliters of a methanol solution containing 0.6 g (16.0 mmol) of $NaBH_4$ is added dropwise to 10 ml of a methanol solution containing 2.0 g (14 7 mmol) of 2-methoxybenzaldehyde, followed by stirring at room temperature for about 1 hour. After the progress of reaction has been confirmed by thin-layer chromatography, 100 ml of water is poured into the reaction solution to decompose excess $NaBH_4$, followed by extraction with three 30 ml portions of ether. The ether layer is dried over anhydrous $Na_2SO_4$, and then filtered. When the solvent is removed by distillation, 1.95 g (yield: 96.1%) of 2-methoxybenzyl alcohol is obtained as an oily colorless product.

(2) In 20 ml of anhydrous benzene, 1.75 g (12.7 mmol) of 2-methoxybenzyl alcohol is dissolved, and the solution is stirred at 0° C. (on an ice bath) for about 20 minutes with blowing HBr gas therethrough.

After reflux of the reaction solution for 2 hours, benzene is removed by distillation under reduced pressure. The product is separated by silica gel column chromatography [$SiO_2$: 200 g, hexane-ethyl acetate (96:4)], and recrystallized from methanol, thereby obtaining 0.86 g (yield: 33.8%) of 2-methoxybenzyl bromide as white crystals.

(3) To 450 mg (2.2 mmol) of 2-methoxybenzyl bromide, 0 7 ml ($4.1 \times 10^{-3}$ mol) of excess triethyl phosphite is added, and the mixture is stirred at 130° C. for about 1 hour until no further evolution of ethyl bromide is observed. After reaction, excess triethyl phosphite is removed by distillation under reduced pressure. 2-Methoxybenzyl phosphonate (a-2) (630 mg) obtained as an oily brown residue is used in the subsequent Wittig-Horner reaction without purification. This reaction is assumed to have proceeded quantitatively.

Wittig-Horner Reaction

In an atmosphere of nitrogen, 4 ml of anhydrous N,N-dimethylformamide is added to 630 mg (2.2 mmol) of 2-methoxybenzyl phosphonate (a-2) placed in a reaction flask. To the resulting mixture, 150 mg (2.8 mmol) of sodium methoxide is added with cooling at 0° C. on an ice bath. Subsequently, 0.3 ml (2.5 mmol) of 4-methoxybenzaldehyde is added dropwise thereto. The mixture is stirred at 0° C. for 1 hour, and further stirred overnight at room temperature.

Twenty milliliters of water is added to the reaction solution, followed by extraction with three 20 ml portions of ethyl acetate. The ethyl acetate layer is washed with two 5 ml portions of water and dried over anhydrous $Na_2SO_4$, followed by concentration under reduced pressure, thereby obtaining 1.3 g of a crude product. When this crude product is purified by silica gel column chromatography [$SiO_2$: 50 g, hexane-ethyl acetate (9:1)], 349 mg (yield: 74.7%) of 2,4'-dimethoxystilbene (c-2•4, sample No. 21) is obtained as white crystals.

Demethylation Reaction

To 80 mg (0.33 mmol) of 2,4'-dimethoxystilbene, 200 mg (1.7 mmol) of pyridinium chloride is added, and the mixture is stirred at 170° C. for 3 hours. After allowed to cool, the mixture is cooled on an ice bath, and 2 ml of a 2M aqueous solution of HCl is added thereto. The resulting mixture is extracted with three 20 ml portions of ether, and the ether layer is dried over anhydrous $Na_2SO_4$, followed by filtration. The solvent is removed by distillation under reduced pressure, thereby obtaining a reaction mixture. The mixture is separated into dihydroxy and monohydroxy forms by silica gel column chromatography [$SiO_2$: 50 g, hexane-ethyl acetate (9:1→8:2)]. When the monohydroxy form is further isolated by high performance liquid chromatography [Wakopack Wakosil, hexane-ethyl acetate (9:1)], 5.13 mg (yield: 6.8%) of 2-hydroxy-4'-methoxystilbene (d-2 4, sample No. 22) is obtained as colorless needle crystals (melting point: 142°-143° C.).

A pale yellow oily product of 2-hydroxy-3'-methoxystilbene (sample No. 19) and powdery colorless crystals (melting point: 78° to 79° C.) of 3-hydroxy-3'-methoxystilbene (sample No. 26) are also synthesized in a manner similar to that used in the synthesis of 2-hydroxy-4'-methoxystilbene (sample No. 22) described above.

The nematicides containing these compounds having the nematicidal activity as main ingredients contain these active ingredients in an amount of about 1 to 10%, in combination with other known carriers, etc.

As the carriers of the pest control chemicals including the repellents and the nematicides for the pine wood nematodes, liquid carriers or solid carriers are used depending on the purpose of their use.

The liquid carriers include water, alcohols, ketones, ethers, aromatic hydrocarbons, acid amides and esters. The solid carriers include known solid carriers such as mineral powders, alumina, sulfur powder and active carbon.

For the formulation, the pest control chemicals can be used as injection and catapasm. These preparations may contain emulsifiers, suspensions, stabilizers, stickers, penetrants and dispersing agents, if necessary, and can be prepared by methods known in the art.

EXAMPLE 1

Repellent

A dust formulation or a liquid formulation containing 1 to 2% of the α-humulene ingredient in combination with another known carrier is prepared.

EXAMPLE 2

Nematicide 1 to 2% of the methyl ferulate ingredient is dissolved in an organic solvent, and the solution was enclosed in ampoules to prepare an injection formulation with which tracheids of pine trees are injected.

EXAMPLE 3

Each of the hydroxystilbenes is dissolved in an organic solvent at 1 to 2%, and the solution is enclosed in ampoules to prepare an injection formulation with which tracheids of trees are injected.

The hydroxystilbenes are highly effective as pest control chemicals against pine wood nematodes.

What is claimed is:

1. A process for preparing a hydroxystilbene or a salt thereof, said process comprising:
   reacting a benzyl phosphonate and a methoxybenzaldehyde in the presence of a base by Wittig-Horner reaction to form a methoxystilbene; and
   conducting a demethylation of the resulting methoxystilbene in the presence of Lewis acid to form the hydroxystilbene or the salt thereof.

2. The method for controlling pine wood nematodes in wood, said method comprising treating the wood with an effective amount of a nematode control chemical comprising an extract from a pine tree with an organic solvent, the extract having pine wood nematode repellant activity or nematicidal activity.

3. The method of claim 2, further comprising selecting said pine tree from the group consisting of an Eastern white pine, a Longleaf pine, a Shortleaf pine, a Loblolly pine, a *Pinus effiottii* L., a Pitch pine and a Formosan masson pine.

4. The method of claim 2, further comprising selecting said organic solvent from the group consisting of an alcohol, a hydrocarbon, a chlorinated hydrocarbon, an acetate ester and a ketone.

5. A method for controlling pine wood nematodes in wood, said method comprising treating the wood with a repellent comprising a carrier containing a pine wood nematode repellent effective amount of α-humulene or a mixture of α-humulene and β-bisabolene.

6. A method for controlling pine wood nematodes in wood, said method comprising treating the wood with a repellant comprising a carrier containing a pine wood nematode repellant effective amount of a mixture of α-pinene and calarene.

7. A method for controlling pine wood nematodes in wood, said method comprising treating the wood with a nematicide comprising a carrier containing a pine wood nematicidal effective amount of methyl ferulate, (+)-pinoresionol, or a mixture thereof.

8. A method for controlling pine wood nematodes in wood, said method comprising treating the wood with a composition comprising a carrier containing a pine wood nematode controlling effective amount of a hydroxystilbene or a salt thereof.

9. The method for controlling pine wood nematodes as set forth in claim 8, wherein said hydroxystilbene or said salt thereof is pinosylvin monomethyl ether, pinosylvin monomethyl ether sodium salt, pinosylvin monomethyl ether potassium salt, 3-hydroxystilbene, 3-hydroxystilbene sodium salt, 3-hydroxystilbene potassium salt, 2-hydroxystilbene, 2-hydroxystilbene sodium salt, 2-hydroxystilbene potassium salt, 4-hydroxystilbene, 4-hydroxystilbene sodium salt, 4-hydroxystilbene potassium salt, 2,3'-dihydroxystilbene, 3-hydroxy-3'-methoxystilbene, 2-hydroxy-3'-methoxystilbene or 2-hydroxy-4'-methoxystilbene.

* * * * *